US00PP12739P2

(12) United States Plant Patent
Winchel

(10) Patent No.: US PP12,739 P2
(45) Date of Patent: Jul. 2, 2002

(54) HYBRID TEA ROSE PLANT NAMED 'WINGOLD'

(75) Inventor: Joseph F. Winchel, Harbor City, CA (US)

(73) Assignee: Coiner Nursey, LaVerne, CA (US)

( * ) Notice: Subject to any disclaimer, the term of this patent is extended or adjusted under 35 U.S.C. 154(b) by 0 days.

(21) Appl. No.: 09/483,455

(22) Filed: Jan. 12, 2000

(51) Int. Cl.[7] ..... A01H 5/00
(52) U.S. Cl. ..... Plt./134
(58) Field of Search ..... Plt./134, 130

*Primary Examiner*—Bruce R. Campell
*Assistant Examiner*—June Hwu
(74) *Attorney, Agent, or Firm*—Christie, Parker & Hale, LLP

(57) ABSTRACT

A hybrid tea rose plant variety producing yellow flowers.

1 Drawing Sheet

BACKGROUND OF THE INVENTION

The present invention relates to a new and distinct hybrid tea rose variety which was originated by my crossing as seed parent the variety known as 'Gold Medal,' U.S. Plant Pat. No. 5,177, and an undistributed, unnamed, unpatented seedling as pollen parent. The varietal denomination of this new rose is 'Wingold'.

SUMMARY OF THE INVENTION

Among the novel characteristics possessed by the new variety which distinguish it from its parents and all other varieties of which I am aware are its attractive yellow flowers.

Asexual reproduction by budding of the new variety as performed outdoors in Kern County. Calif., shows that the foregoing and other distinguishing characteristics come true to form and are established and transmitted through succeeding propagations. Other known forms of asexual reproduction may be also used.

COMPARISON WITH PARENT

New variety differs from its undistributed pollen parent in flower color and size.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

The following is a detailed description of the new two years old variety, from specimens grown in Kern County, Calif., in the month of November. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

Flower:

*Habit.*—Recurrent.

*Bud.*—Size: Length about ⅞ inch width about ¾ inch. Form: Elongated. Color: When sepals first divide near 14A.

*Sepals.*—About 1¾ inches in length; longer than bud, color near 194A.

*Peduncle.*—Length: About ⅝ inch. Strength: Erect, sturdy. Color: Near 143C.

*Bracts.*—None apparent.

Bloom:

*Size.*—About 4 inch diameter.

*Borne.*—Singly.

*Form.*—High centered at first, becoming flat.

*Petalage.*—About 23, imbricated, top surface satiny, under surface dull.

*Color (⅓ to ½ open).*—Outer petals: Top surface near 16A; under surface near 16B. Inner Petals: Top surface near 16A; under surface near 16B. Base of petals: Near 16B. General tonality from a distance: Near 16B.

*Color (fully open).*—Outer petals: Top surface near 11C; undersurface near 11D. Inner petals: Top surface near 11C. Base of petals: Near 11D. General tonality from a distance: Near 11D.

*Color change.*—Fades to near 11D.

*Appearance.*—Velvety.

*Form.*—Oval.

*Arrangement.*—Imbricated, shingle-like.

*Petaloids in center.*—About 2 to 3.

*Persistence.*—Petals drop off cleanly.

*Fragrance.*—Slight.

*Size.*—Petals are about 1¼ inches long by about 1½ inches wide.

*Lastingness.*—Flowers last about 10 to 14 days on the plant and about 3 days after cutting.

Reproductive organs:

*Stamens, filaments and anthers.*—Arrangement: Regularly arranged. Color Stamens: Near 66C. Anthers: Near 20D, about 68.

*Pollen.*—Color: Near 23D.

*Styles.*—Uneven.

*Stigmas.*—Color: Near 14A. Pistils: About 62.

*Hips.*—Globular, about 1 to 1¼ inches, near 16B, seeds do not protrude.

Plant:

*Form.*—Upright.

*Growth.*—Very vigorous, about 36 inches after first season.

*Foliage.*—Compound 5 leaflets, leaf tip and apex are acute and not unusual in this plant. Size: About 2 5/16 inches long by about 1½ inches wide. Quantity: Abundant. Color New foliage: Upper side near 146C; underside near 146D. Old foliage: Upper side near 141A; underside near 141D. Shape: Elliptical. Texture: Smooth. Edge: Serrated. Serration: Serrate (fine). Disease Resistance: Very resistant to mildew, blackspot and rust. Auricle: Short pointed.

*Wood.*—New shoots: Near 152C, smooth. Old wood: Near 135C, smooth.

*Thorns.*—Quantity: Few, about 5 to 6 per branch. Form: Curved downward. Length: Medium. Color when young: Near 161A. Position: Regular.

*Prickles.*—Almost none.

*Flower stems.*—About 2¼ inches.

Winter hardiness: Completely winter hardy in Kern County, Calif.

I claim:

1. A new and distinct hybrid tea rose plant of the variety substantially, as shown and described.

* * * * *

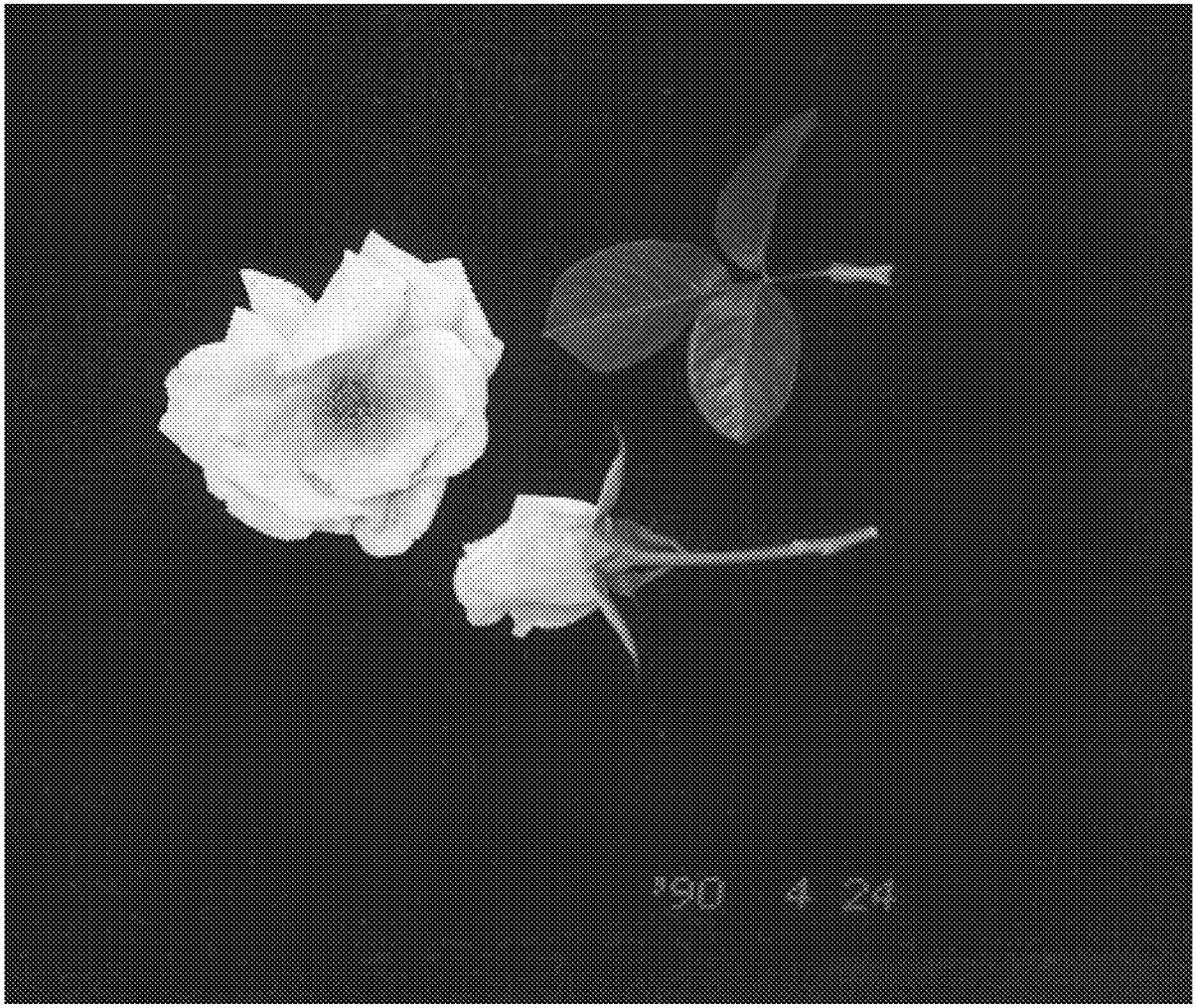
'90 4 24